United States Patent [19]

Hsia

[11] 4,240,797
[45] Dec. 23, 1980

[54] ASSAY FOR RESERVE BILIRUBIN BINDING CAPACITY

[75] Inventor: Jen C. Hsia, Don Mills, Canada

[73] Assignee: The Governing Council of the University of Toronto, Toronto, Canada

[21] Appl. No.: 843,490

[22] Filed: Oct. 18, 1977

[51] Int. Cl.³ .................... G01N 23/48; G01N 24/00
[52] U.S. Cl. .................................... 23/230 B; 23/905;
23/911; 260/326.46; 548/215; 548/225;
548/233; 546/223; 546/248
[58] Field of Search ...................... 23/230 B, 905, 911

[56] References Cited

U.S. PATENT DOCUMENTS

| | | | |
|---|---|---|---|
| 3,453,288 | 7/1969 | McConnell | 23/230 R |
| 3,706,537 | 12/1972 | Becher | 23/230 R |
| 3,716,335 | 2/1973 | Ullman | 23/230 R |
| 3,730,687 | 5/1973 | Rondeau | 23/230 R |
| 3,915,641 | 10/1975 | Goering | 23/230 R |

OTHER PUBLICATIONS

G. B. Odell, J. Pediat., 68, 164–180, (1966).
E. G. Porter, et al., J. Lab. Clin. Med., 67, 660–667, (1966).
C. L. Hamilton, et al., "Spin Labels", Chapt. in Structural Chemistry and Molecular Biology, A. Rich, et al., eds., pp. 115–147, W. H. Freeman Co., 1968.
J. C. Hsia, et al., J. Immunol. Meth. 3, 17–24, (1973).

Primary Examiner—Sidney Marantz
Attorney, Agent, or Firm—Ridout & Maybee

[57] ABSTRACT

Spin labels, especially dianionic aromatic spin labels which can bind to the first specific high-affinity bilirubin-binding site on serum albumin, and which are quantitatively displaceable into solution from said site in the presence of bilirubin, can be used in an assay for bilirubin-binding capacity. In the assay, an excess of spin label is mixed with the serum albumin or serum and is titrated with standard bilirubin. ESR spectroscopy indicates a change in the rate of spin label release with addition of bilirubin, giving a value indicative of bilirubin-binding capacity. Novel dianionic aromatic spin labels are also disclosed.

9 Claims, 2 Drawing Figures

ASSAY FOR RESERVE BILIRUBIN BINDING CAPACITY

BACKGROUND OF THE INVENTION

The invention relates to methods for determining values relating to the reserve bilirubin-binding capacity of serum albumin containing aqueous specimens, and to compositions for use in such methods.

It is known that serum albumin has two high-affinity bilirubin-binding sites. For the first specific bilirubin-binding site the association constant for the reversible binding of bilirubin, $K_{assoc.}$, is of the order of $10^8$ liters/mole. For the second specific bilirubin-binding site, the association constant $K_{assoc.}$ is of the order of $10^6$ liters/mole.

It is of interest to the clinician to determine a value for the reserve bilirubin-binding capacity that represents the proportion of the said first specific high-affinity bilirubin-binding sites that are available for binding bilirubin. This is especially important in the neonatal care of jaundiced newborns.

By "reserve bilirubin-binding capacity" is meant the reserve binding-capacity of the first specific high affinity bilirubin site of serum albumin, the maximum value of this capacity being 1. The blood of the jaundiced newborn contains excessively high levels of bilirubin. When the reserve bilirubin-binding capacity of the serum albumin is low, bilirubin may find its way into the brain of the new born and cause permanent damage which may required institutional care of the patient for the rest of his life. The only method which is available for avoiding this condition is blood transfusion, and such transfusions have to be made well before the reserve bilirubin-binding capacity becomes depleted, to avoid the possibility of permanent brain damage. At present, there is no satisfactory method for determining the reserve bilirubin-binding capacity. A satisfactory assay method would therefore be highly desirable and of important assistance to the care of new borns and especially in indicating when a blood transfusion is called for.

Known methods for determining the reserve bilirubin-binding capacity, such as the peroxidase technique, electrophoretic methods, Sephadex filtration, fluorescent techniques, and methods using dyes to duplicate the binding of bilirubin to albumin, are subject to various disadvantages. For instance, some of these methods require too large an amount of blood for each test, and so they cannot be used for following the rise and fall of the binding capacity since repeated tests would demand the withdrawal of an excessive quantity of blood from the neonate body. The methods that rely on dyes and on observing colorimetric changes cannot be applied to hemolysed blood samples, as the resultant coloration obscures the color changes that are to be observed.

SUMMARY OF THE INVENTION

The present invention provides a simple, accurate, and convenient assay for determining the reserve bilirubin-binding capacity of serum albumin which is, moreover, particularly advantageous in newborns because it requires only very small amounts of blood. The present invention also provides new spin labels which are singularly useful in the above assay.

The present invention uses a spin label in an assay method for determining the reserve binding capacity. The term "spin label" is well known and refers to relatively stable, water-soluble compounds that include within their molecule the structure of a free radical containing an unpaired electron.

Examples of typical spin labels include tetramethyl-substituted nitroxides of formula

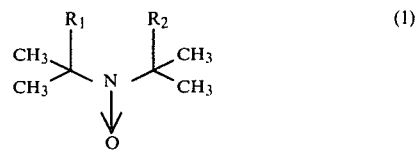

wherein $R_1$ and $R_2$ may complete a ring system. A large number of such compounds have been described in the literature. Spin labels that are useful for some previously known purposes are capable of binding reversibly to large molecules, e.g. proteins. By employing electron spin resonance spectroscopy it is possible to determine to a high degree of accuracy the amount of free and bound spin label in an aqueous solution containing a known amount of spin label and a molecule to which the label binds. On subjecting a sample of the solution to ESR spectroscopy, distinct spectral peaks resulting from the presence of free spin label are obtained. The height of these peaks, or, more rigorously, the area under the peaks, is proportional to the concentration of free spin label in the solution. Thus, by comparison with standard solutions of spin label, the amount of free spin label in the sample under test can be determined. The amount of bound spin label can then be obtained by subtraction from the total amount originally added.

Some spin labels have now been found that bind to the first specific high-affinity bilirubin-binding site of serum albumin and are quantitatively displaceable from this binding sites into solution on addition of bilirubin to the albumin. By "quantitative displacement" the present applicant refers to a displacement of spin label into solution which is proportional to the amount of bilirubin added. Moreover, the present applicant has found some new spin labels that have the desirable property of relatively strong affinity for the said first specific high-affinity bilirubin-binding site and have relatively high selectivity for binding at these sites, that is to say they have significantly larger affinity for the first specific high-affinity bilirubin-binding site than for other bilirubin-binding sites on the serum albumin molecule such as the second high-affinity bilirubin-binding sites and non-specific binding sites.

The assay method of this invention uses spin labels that bind to the first specific bilirubin-binding site of serum albumin, and which are quantitatively displaceable, on addition of bilirubin, from the said site into the solution, where their presence can be detected by the above-described ESR spectroscopy procedures.

In the assay method, a molar excess of the spin label is added to the serum albumin-containing sample, this excess amount of spin label being sufficient to occupy most of the available first specific high-affinity bilirubin-binding sites that are not previously occupied. The molar concentration of serum albumin in the specimen may be previously determined, using conventional methods, prior to conducting the assay. In theory, it should be sufficient to add 1 mole of spin label per mole of serum albumin, but in practice it is found that superior results are obtained when at least 3 moles of spin label per mole of serum albumin are added to the specimen. If lesser quantities of spin lable are added, the discontinuity in the spin label displacement curve, which will be described later, is found to be less sharp. Too great an excess should not be added, however, since this will tend to mask the subsequent increase in free spin label concentration resulting from displacement of the bound spin label into the solution. An amount in the range of about 3 to 6 mole of spin label per mole of serum albumin is preferred, more preferably about 4 to 5 mole per mole of serum albumin.

The specimen containing the excess spin label is then titrated with a standard bilirubin solution, and is subjected to ESR spectroscopy. Instead of adding increasing amounts of bilirubin to a single volume of the specimen, it will normally be more convenient to divide the specimen into aliquots and add a progressively greater quantity of the bilirubin to each. With addition of bilirubin, the amount of free spin label displaced into solution increases in proportion to the amount of bilirubin added, and this progressive increase can be followed by observing the height of the ESR spectral peak associated with free spin label. At a certain level of bilirubin addition, there occurs a discontinuity in the progressive release of free spin label, and beyond this level the rate of release of spin label with increasing bilirubin addition slows considerably. Thus, when the displacement of spin label is graphed against the molar ratio of bilirubin to serum albumin, there is a discontinuity in the curve. At this region of discontinuity, the first specific high-affinity sites of the serum albumin molecules have been occupied by the added bilirubin, which has replaced the spin label that was formerly bound. The remainder of the curve indicates displacement from sites other than the first specific binding site. Thus, the region at which this discontinuity occurs can serve to indicate what proportion of the first specific bilirubin-binding sites in the albumin of the specimen were unoccupied and available for binding with bilirubin.

In examining spin labels for their suitability for use in the above assay, the potentiality of the spin label for binding at the high-affinity bilirubin-binding sites can be investigated by mixing a standard solution of serum albumin, obtained in a form free from bilirubin with increasing amounts of the spin label, determining the proportions of free and bound spin label by the ESR techniques described above, and repeating the procedure using serum albumin to which has been added one equivalent of bilirubin per mole of albumin.

The procedures used and ESR techniques that may be used in the above investigation are in themselves generally known to those skilled in the art and need not be described in detail here. See Scatchard, G. (1949) Ann. N.Y. Acad Sci, 51, 660 to 672 and Swartz et al. (1972) Biological Applications to Electron Spin Resonance, Wiley-Interscience, New York. In analysing the data that are obtained, the conventional procedure of preparing a Scatchard plot may be followed. From the Scatchard plots, for the solutions with and without added bilirubin, an indication of the affinity from the spin label for the said first specific high-affinity bilirubin-binding site can be obtained. In an example of a suitable spin label, e.g. the compound TOPA-DNB described in more detail later, a Scatchard plot shows that the label has two binding sites on serum albumin, and that the first specific high affinity binding site is blocked on addition of bilirubin. The binding will in such case typically have two association constants associated with it, one of high affinity and one of lower affinity. From this it can be deduced that first specific high affinity binding site for the spin label is the first specific high affinity binding site for bilirubin.

From the data that are obtained in the above procedures, the $K_{assoc.}$ for the binding of the spin label to its first specific high affinity binding site can be obtained.

Preferably in the assay method of the invention there are used spin labels that exhibit a $K_{assoc.}$ for the first specific high-affinity site of not less than about $10^3$ liters/mol. At values much less than $10^3$ liters/mol, the amount of spin label that binds to the serum albumin, and that will be displaced into solution on addition of bilirubin during the assay, may in some circumstances be so small that the increase in free spin label concentration in the assay solution is insufficient to yield a reliable determination of the binding capacity.

The specificity of the spin label for binding at the first specific high-affinity sites as opposed to the second bilirubin-binding sites and non-specific binding sites can be investigated by taking a normal, bilirubin-free, serum albumin sample containing a known quantity of albumin, adding a suitable excess of the spin label and titrating the mixture with bilirubin while observing the displacement of bound spin label from the albumin through the ESR spectroscopic technique discussed above. An example of such an investigation is described in more detail later. With spin labels that exhibit good specificity, the displacement of spin label is proportional to the addition of bilirubin up to a region of discontinuity beyond which lesser quantities of free label are displaced. With spin labels that do not bind selectively to the first specific high-affinity sites in the presence of bilirubin but also bind readily to the second and non-specific binding sites, there is no proportionality between the displacement of spin label and the addition of bilirubin, and a discontinuity in the increase in free spin label concentration is not observable through ESR spectroscopic methods.

DESCRIPTION OF THE PREFERRED EMBODIMENTS

Figure 1:
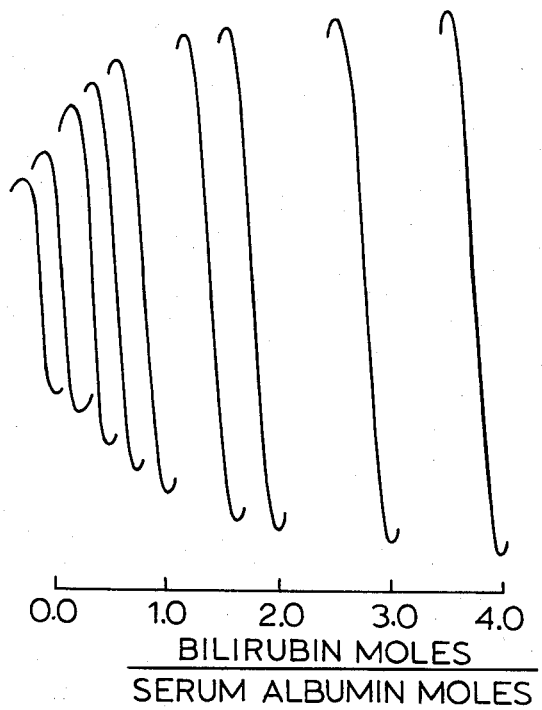

Some examples of preferred spin labels that can be employed in the assay can now be given.

It has been found that spin labels that are dianionic compounds exhibit markedly superior selectivity for binding at the first specific high-affinity site. Examples include dicarboxylic acids, diphenols or compounds that contain both phenolic and carboxylic groups. Without wishing to rely on any particular theoretical explanation, it is suggested the superiority of the dianionic compounds may be due to their ability to mimic the bilirubin molecule, which has two propionic acid residues in its structure.

Thus, for example, the known, mono-anionic, spin label 5-N (2,2,6,6-tetramethyl-1-oxyl-4 aminopiperidinyl) 2,4-dinitrophenol, referred to herein as TOP-DNP, of formula

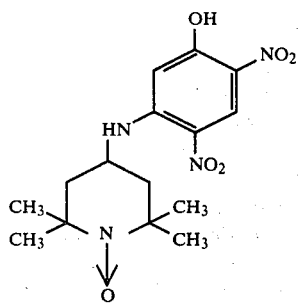

(2)

is, in its phenate form, bound to bind strongly to the high-affinity bilirubin-binding sites, but when tested for specificity it is found that this spin label is not quantitatively displaced into solution on addition of bilirubin, but instead is re-bound at binding sites other than the high-affinity binding sites.

Examples of useful dianionic spin labels that are preferably used in this invention include water soluble compounds of formula

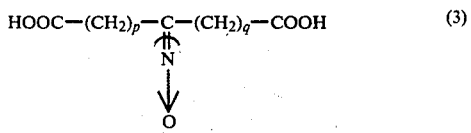  (3)

wherein p and q are each integers of from 0 to 5 and

represents

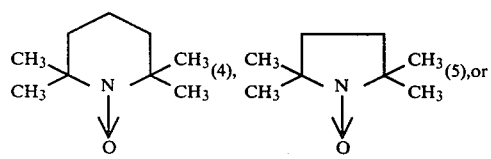 (4), (5), or

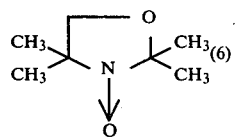 (6)

and water soluble salts and esters thereof. These compounds can be prepared by generally known synthetic preparative procedures for example through reaction of an appropriate dicarboxylic ester with a spin label containing a reactive carbonyl group followed by hydrolysis to yield the monoester of the dicarboxylic acid.

Thus, for example one preferred group of spin labels namely 2,2,6,6-tetramethyl-1-oxyl-4-piperidylidenesuccinic acid, referred to herein as TOPS, and its corresponding monoethyl ester, referred to herein as TOPSE, can be prepared by the following reaction.

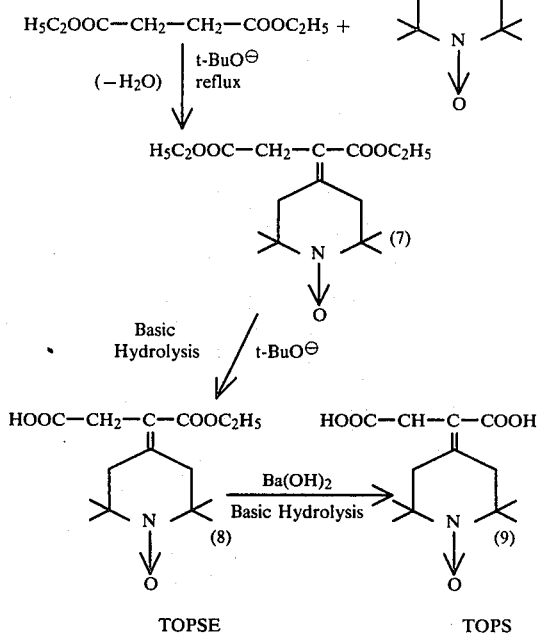

As compared with TOP-DNP the compound TOPS exhibits greater specificity for the high-affinity binding sites and is displaced by bilirubin quantitatively into solution from serum albumin. However, the TOPS compound has a considerably lower $K_{assoc.}$ than TOP-DNP, of the order of $10^3$ liters/mole as compared with a $K_{assoc.}$ of the order of $10^6$ liters/mole for TOP-DNP. It is considered that compounds having an aromatic moiety in their molecular structure exhibit an increased affinity for the bilirubin-binding sites. Thus, the most preferred class of spin labels are novel dianionic compounds containing an aromatic moiety. Examples of this class include compounds of formula

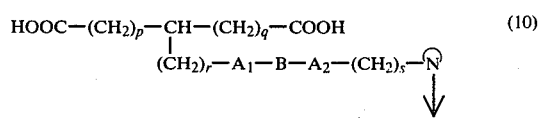 (10)

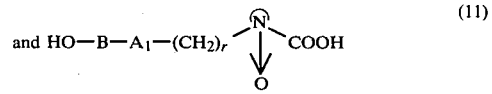 (11)

wherein p, q, and

have the same meanings as above, r and s are integers of 0 to 6, $A_1$ and $A_2$ are NH, S, or O, and B is substituted or unsubstituted phenylene, preferably 1,5-phenylene, or substituted or unsubstituted diphenyl sulfone, and water-soluble salts, phenates and esters thereof.

These compounds are prepared by generally known preparative reactions. For example, compounds of formula (10) wherein B is a 1,5-substituted 2,4-dinitrobenzene or diphenylene sulfone can be prepared by reacting a 1,5-dihalo-2,4-dinitro benzene of the formula

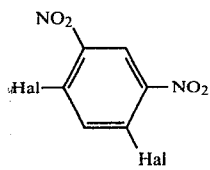 (12)

or 4,4'-dihalo-3,3'-dinitrophenylsulfone of the formula

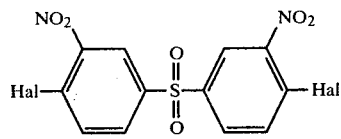 (13)

in which Hal is fluorine, chlorine, or bromine with a spin label of the formula

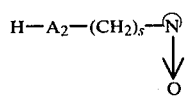 (14)

to obtain a product of the formula

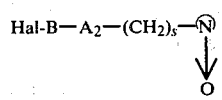 (15)

and reacting the last-named product of formula (15) with a dicarboxylic acid, mercapto, or hydroxy acid of the formula

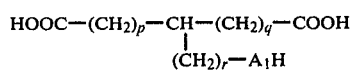 (16)

and isolating the corresponding compound of formula (10).

Dianionic spin labels containing a phenolic group and a carboxylic group are prepared by reacting a spin label containing a carboxylic and an amino, mercapto, or hydroxy group of the formula

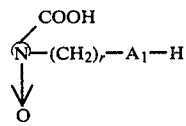 (17)

with a 1,5-dihalo-2,4-dinitrobenzene of the formula (12) or a 4,4'-dihalo-3,3'-dinitro phenylsulfone of the formula (13) and treating the resulting compound of the formula

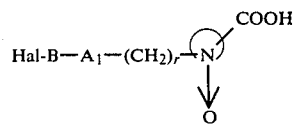 (18)

with base to obtain the corresponding phenolic carboxylic acid as the phenate and carboxylate salt of formula

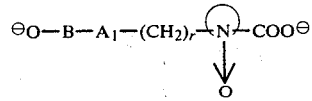 (19)

In each of the above compunds, a product containing a nitro phenylene residue can be reduced to the corresponding phenylene compound by conventional procedures, e.g. reduction of the nitro groups to amine followed by diazotization and reduction with hypophosphorous acid.

One preferred dianionic aromatic spin label is 4-[5-N-(aspartic acid)-2,4-dinitroanilino]-2,2,6,6-tetramethyl-1-piperidinooxyl or 1-N(2,2,6,6-tetramethyl-1-oxyl-4-aminopiperidinyl)-5-N(1-aspartic acid)-2,4-dinitrobenzene, herein referred to as TOPA-DNB, of formula

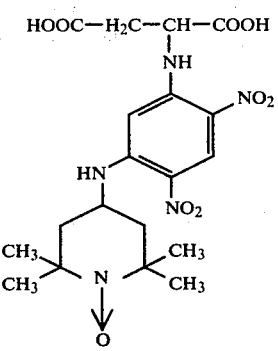 (20)

This compound has relatively strong affinity for the bilirubin-binding sites of serum albumin and the Scatchard plot for the binding of TOPA-DNB to serum albumin in the absence of bilirubin reveals that the binding involves at least two sites and some non-specific binding The $K_{assoc.}$ for the first specific binding site is in the range $10^4$ to $10^5$ liters/mole. In the presence of bilirubin, TOPA-DNB is displaced quantitatively from first specific high-affinity bilirubin binding sites on serum albumin.

EXAMPLE 1

Preparation of 4-(5-fluoro-2,4-dinitroanilino)-2,2,6,6-tetramethyl-1-piperidinooxyl

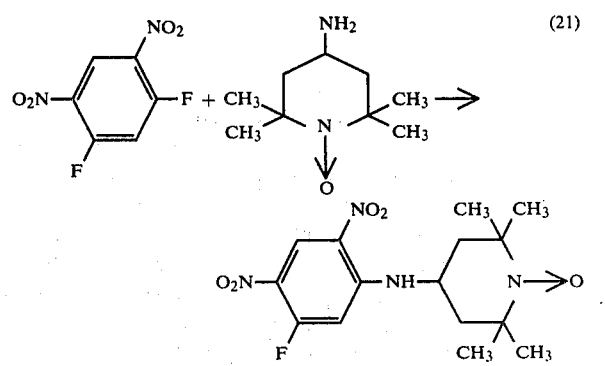 (21)

1 mM of 1-oxyl-2,2,6,6-tetramethyl-4-aminopiperidine in 5 ml of chloroform is added dropwise into 1 mM of 1,5-difluoro-2,4-dinitrobenzene dissolved in 10 ml chloroform. Under vigorous magnetic stirring, it is allowed to react overnight shielded from light. After the solvent is stripped off, a yellow precipitate is chromatographed on a silicic acid column and eluted with chloroform. Fast moving yellow bands are collected and recrystallization is carried out in chloroform and ether and small amount of hexane. m.p. 198.5°-199°.

M.W. calc.: 355.34. Mass spectral analysis found: 355.

EXAMPLE 2

In the same manner as in Example 1, using 1 mM of 1-oxyl-2,2,5,5-tetramethyl-3-aminopyrrolidine in place of the aminopiperidine starting material, there is obtained 3-(5-fluoro-2,4-dinitroanilino)-2,2,5,5-tetramethyl-1-pyrrolidinooxyl.

EXAMPLE 3

In the same manner as in Example 1 using 1,5-dichloro-2,4-dinitrobenzene in place of 1,5-difluoro-2,4-dinitrobenzene there is obtained 4-(5-chloro-2,4-dinitroanilino-)-2,2,6,6-tetramethyl-1-piperidinooxyl.

EXAMPLE 4

Following the same method as in Example 1 and using 2,2,4,4-tetramethyl-3-oxyl-5-amino-1-oxazolidine in place of the aminopiperidine starting material, there is obtained 5-(5-fluoro-2,4-dinitroanilino)-2,2,4,4-tetramethyl-1-oxazolino-3-oxyl.

EXAMPLE 5

Following the method of Example 1 and using 1-oxyl-2,2,6,6-tetramethyl-4-hydroxy-piperidine instead of 1-oxyl-2,2,6,6-tetramethyl-4-aminopiperidine there is obtained 4-(5-fluoro-2,4-dinitroanilino)-2,2,6,6-tetramethyl-1-piperidinooxyl.

EXAMPLE 6

Following the method of Example 1 and using 1-oxyl-2,2,6,6-tetramethyl-4-mercaptopiperidine (hypothetical compound) instead of 1-oxyl-2,2,6,6-tetramethyl-4-aminopiperidine there is obtained 5-(5-fluoro-2,4-dinitro-thiobenzene)-2,2,6,6-tetramethyl-1-piperidinooxyl.

EXAMPLE 7

Employing 1,5-dibromo-2,4-dinitrobenzene in place of 1,5-difluoro-2,4-dinitrobenzene in the method of Example 1, there is obtained 4-(5-bromo--2,4-dinitrobenzene)-2,2,6,6-tetramethyl-1-piperidinooxyl.

EXAMPLE 8

Employing 4,4'-dichloro-3,3'-dinitrophenyl sulfone instead of 1,5-difluoro-2,4-dinitrobezene in the method of Example 1, there is obtained N-(2,2,6,6-tetramethyl-1-oxyl-4-piperidinyl)-4-amino-4'-chloro-3,3'-dinitrophenyl-sulfone.

EXAMPLE 9

Preparation of the spin label formula (20)

L-Aspartic acid (399 mg, approx. 3 mM) and $Na_2CO_3$ (972 mg, approx. 9 mM) are dissolved in 25 ml of 40% aqueous ethanol solution. To this solution is added 4-(5-fluoro-2,4-dinitroanilino)-2,2,6,6-tetramethyl-1-piperidinooxyl of formula (21) (355 mg, 1 mM, prepared as in Example 1 above. The mixture is heated at 45°-50° C. overnight with stirring. The reaction mixture is cooled and diluted with $H_2O$ (15 ml) and filtered. The filtrate is extracted with $CHCl_3$ (2×30 ml). The aqueous layer is then acidified with dilute HCl (0.5 N) and precipitation occurs. The yellowish precipitate is filtered and washed with $H_2O$ until it is free of acid and then dried in air. The product is recrystallized from $DMSO/H_2O$ to give 250 mg of yellow crystals & yield 53%; $R_f$ value = 0.56 (on silica gel with a solvent system $CHCl_3$:$CH_3OH$:acetic acid, 80:20:2); m.p. = 220° C. (decomposed); UV, λmax = 339 and 420 nm (respective molar extinction coefficients of 28,000 and 10,700) for a methanol solution of TOPA-DNB as a disodium salt, I.R. prominent features, 3350 $cm^{-1}$ (—NH stretching), 1720 $cm^{-1}$ (carboxylic acid >C=O stretching), 1570 and 1330 $cm^{-1}$ (conjugated nitro-group), 3200-2500 $cm^{-1}$ (—OH stretching); could not obtain parent ion in mass spectrum.

EXAMPLES 10 to 16

In the same manner, employing the products of Examples 2 to 8 in place of the compound of formula (21) there are obtained the following products, respectively.

EXAMPLE NO.

10. 3-[5-N-(aspartic acid)-2,4-dinitroanilino]-2,2,5,5-tetramethyl-1-pyrrolidinooxyl.
11. Compound of formula (20).
12. 5-[5-N-(aspartic acid)-2,4-dinitroanilino]-2,2,4,4-tetramethyl-1-oxazolidino-3-oxyl.
13. 4-[5-N-(aspartic acid)-2,4-dinitroanilino]-2,2,6,6-tetramethyl-1-piperidinooxyl.
14. 4-[5-N-(aspartic acid)-2,4-dinitro-thiobenzene]-2,2,6,6--tetramethyl-1-piperidinooxyl.
15. N-[N'-(2,2,6,6-tetramethyl-1-oxyl-4-piperidinyl)4-amino-3,3'-dinitro-4'-diphenylsulfone] aspartic acid.

EXAMPLE 17

Determining specificity of spin label and example of assay

The procedure is conducted under a minimal amount of light to avoid photo-degradation of the bilirubin.

Initially, the bilirubin to be employed is converted to bilirubin disodium salt.

0.24 mg of bilirubin (obtained from Sigma Co., No. B.4126, derived from Bovine gall stones; crystalline) is weighed into a test tube (3 ml). 2 ml of 0.00044 M NaOH in methanol is pipetted into the test tube. The tube is swirled gently until all the bilirubin has dissolved and undissolved bilirubin is filtered through glass wool to obtain a clear bilirubin solution.

A quantitative bilirubin stock solution is then prepared from the solution of disodium salt. With a 25λ (micro liter) Hamilton syringe, 20λ of the bilirubin disodium solution is pipetted into a test tube (3 ml), and the solution is then evaporated to dryness under nitrogen. A 2 ml aliquot of 0.1 M phosphate buffer at pH 7.4 is pipetted into the dried bilirubin disodium salt sample. The concentration of bilirubin in this solution is determined using the known extinction coefficient of bilirubin. The determination is performed with a Unicam SP1800, Spectrophotometer. All measurements are done in triplicate.

The same absorbance should be taken immediately, and the sample removed from the cuvette holder within 30 seconds. Serum is obtained by centrifugation of the coagulated blood of an adult male volunteer, and the concentration of serum albumin is determined by conventional methods. For convenience, the serum is then diluted with 100 mM phosphate buffer pH 7.4 to achieve a convenient serum albumin concentration of $5 \times 10^{-5}$ M.

Appropriate amounts of the bilirubin stock solution are then pipetted into twelve numbered test tubes so that a range of bilirubin to albumin molar ratio from 0 to 2.0 will be obtainable on addition of a constant volume (50λ) of diluted buffered serum to each tube.

The whole set of tubes can then be dried under vacuum, if desired or stored in freezer below 0° C.

To a test tube containing a constant amount of dried TOPA-DNB, prepared from stock TOPA-DNB solution, and dried under nitrogen, a fixed volume (700λ) of the diluted serum sample is added to give a TOPA-DNB to albumin molar ratio of 5:1. The TOPA-DNB and albumin solution is left to stand for 15 minutes. 50λ of the TOPA-DNB/albumin solution is pipetted into each of the twelve numbered test tubes containing the bilirubin, making sure that all the dried bilirubin has dissolved. Each titration sample is then filled into a 25λ micro-pipette (Clay Adams, Micro Pet, Recorder No. 4619) by suction. The sealed micropipettes are subjected to ESR measurements.

A Varian E-6 X-band ESR spectrometer is used. The instrument settings are as follows:

(a) Gain: a convenient setting (1250–3200) is selected within the limits of the microprocessors.
(b) Frequency/power: 9.065 GHZ/40 mw
(c) Modulation (Grass): 2.5
(d) T.C./S.T. (sec/min) 0.3/4.0
(e) Field and Range: 3230±20 Gauss
(f) Temp.: 22°±1° C.

Some of the free TOPA-DNB signals that are obtained are shown in FIG. 1. Each of these peaks is a peak associated with free spin label and its height is proportional to the amount of free spin label in solution. The peak heights are calibrated against known standard solutions of TOPA-DNB and the percent increase in free TOPA-DNB is plotted against the mole percent of added bilirubin or in mg% which yield the reserve bilirubin loading capacity.

Figure 2:
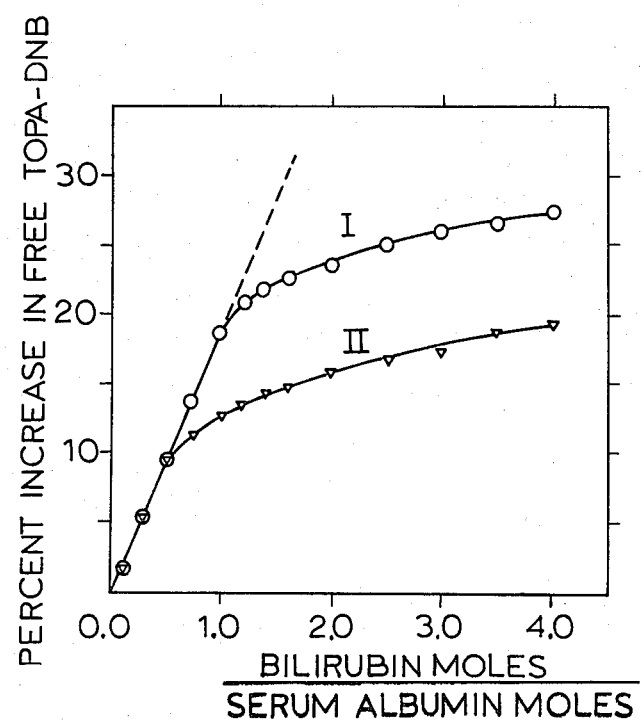

The result is as shown in FIG. 2 (curve I). As shown, at bilirubin levels of up to 1 mole per mole of albumin, the displacement of spin label into the solution is linear.

In order to demonstrate an assay procedure, the above is repeated using serum to which has been added 0.5 equivalent of bilirubin (0.5 mole) per mole of albumin. The result is as shown by curve II. The region of discontinuity of the curve has been shifted left-wards by the presence of bilirubin in the serum specimen, the shift indicating the extent to which the first specific high-affinity bilirubin-binding site is occupied in the specimen.

In the case of the specimen assayed in curve II, the reserve bilirubin-binding capacity is indicated as being smaller than the maximum possible by an amount of 0.5 equivalent of bilirubin.

In the application of assay, if the albumin concentration of the serum sample is known, an absolute value representing the reserve bilirubin-binding capcity (RBBC) can then be obtained from the region of discontinuity on the TOPA-DNB displacement curve. However, if the albumin concentration is not available, the percent increase in free TOPA-DNB is then plotted against the added bilirubin in mg per 100 ml of specimen, the region of discontinuity of the displacement curve is defined as the reserve bilirubin loading capacity (RBLC) in units of mg per 100 ml of specimen. This value can be calculated but is not illustrated in FIG. 2.

The assay method described above has the advantages that since free radicals are rare in physiological specimens, there is little risk of spurious values being obtained from any extraneous contribution to the ESR spectral peaks, it can be applied to cloudy or hemolyzed serum specimens, the assay takes advantage of the complete and instantaneous separation of the bound and free spin labels so that there is instantaneous determination of the equilibrium state, the spin label is itself relatively stable and does not deteriorate over extensive periods, the position of the resonance peaks on the ESR spectrum indicates whether the peak is associated with a bound or a free spin label, the concentration of free spin label can be quantified directly merely by observation of the spectral peak height, and the volume of specimen required is very small, less than 50λ of serum being needed per test, e.g. when the specimen is diluted with an appropriate diluent, a phosphate buffer, the test is performed with considerably small volume of the specimen.

I claim:

1. Assay method for determining values relating to the reserve bilirubin-binding capacity of a serum albumin-containing aqueous specimen comprising the steps of adding to the specimen a molar excess, in terms of albumin content, of a water-soluble spin label comprising a dianionic compound that binds to the first specific high-affinity bilirubin-binding site on the albumin, and is quantitatively displaceable from that site into solution in the presence of bilirubin, titrating the specimen with a standard bilirubin solution, subjecting the specimen with electron spin resonance spectroscopy, obtaining values indicative of changes in the height of spectral peaks associated with free spin label displacement with increased bilirubin addition, and deriving therefrom values indicative of reserve bilirubin-binding capacity.

2. Method as claimed in claim 1 including the step of determining the serum albumin concentration, and calculating therefrom the quantity of spin label which constitutes an excess of spin label, in terms of albumin content, prior to adding the spin label to the specimen.

3. Method of claim 1 wherein at least 3 moles of the spin label are added per mole of serum albumin present in the specimen.

4. Method of claim 3 wherein about 4 to 5 moles of spin label are added.

5. Method of claim 4 wherein about 5 moles of spin label are added.

6. Method as claimed in claim 1 wherein the spin label is a dianionic compound including an aromatic residue.

7. Method as claimed in claim 1 wherein the spin label is a compound selected from the group consisting of

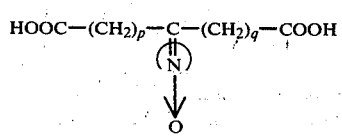

13

-continued

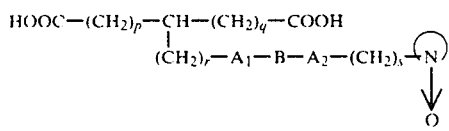

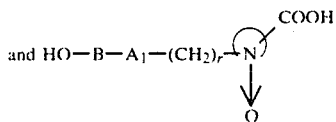

wherein p and q are each integers of from 0 to 5,

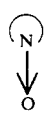

is a group selected from the class consisting of

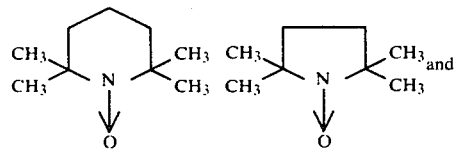

14

-continued

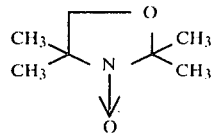

r and s are each integers of from 0 to 6, $A_1$ and $A_2$ are independently selected from the class consisting of NH, S, and O, and B is selected from the class consisting of substituted and unsubstituted phenylene, and substituted and unsubstituted diphenyl sulfone, and water soluble salts and esters thereof.

8. Method as claimed in claim 1 wherein the spin label is a compound selected from the group consisting of 2,2,6,6-tetramethyl-1-oxyl-4-piperidylidene succinic acid of formula

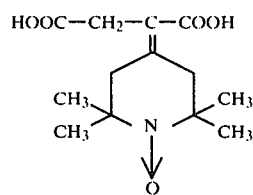

and its water soluble salts and esters.

9. Method of claim 1 wherein the spin label is a compound selected from the group consisting of 1-N(2,2,6,6-tetramethyl-1-oxyl-4-aminopiperidinyl)-5-N(aspartic acid)-2,4-dinitrobenzene and its water soluble salts and esters.

* * * * *